US007422724B1

(12) United States Patent
Manginell et al.

(10) Patent No.: US 7,422,724 B1
(45) Date of Patent: Sep. 9, 2008

(54) BIOLOGICAL PRECONCENTRATOR

(75) Inventors: Ronald P. Manginell, Albuquerque, NM (US); Bruce C. Bunker, Albuquerque, NM (US); Dale L. Huber, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1097 days.

(21) Appl. No.: 10/214,891

(22) Filed: Aug. 7, 2002

(51) Int. Cl.
*G01N 30/96* (2006.01)

(52) U.S. Cl. .............................. 422/88; 96/108; 96/143; 96/154; 422/69; 422/101; 422/102; 436/174; 436/177

(58) Field of Classification Search .................. 96/101, 96/102, 108, 111, 112, 121, 126, 130, 143, 96/154; 422/69, 88, 89, 90, 101, 102; 436/161, 436/174, 177, 178; 95/87, 88, 89, 114, 115
See application file for complete search history.

(56) References Cited

U.S. PATENT DOCUMENTS

| | | | | |
|---|---|---|---|---|
| 3,219,993 | A * | 11/1965 | Schwertz ..................... 345/106 |
| 5,151,110 | A * | 9/1992 | Bein et al. ..................... 95/140 |
| 5,262,127 | A * | 11/1993 | Wise et al. .................... 422/98 |
| 5,385,709 | A * | 1/1995 | Wise et al. .................... 422/98 |
| 5,705,745 | A * | 1/1998 | Treutler et al. ............ 73/204.26 |
| 5,720,798 | A * | 2/1998 | Nickerson et al. ............ 96/102 |
| 6,033,852 | A * | 3/2000 | Andle et al. ................... 435/6 |
| 6,171,378 | B1 | 1/2001 | Manginell et al. |
| 6,393,907 | B1 * | 5/2002 | Yamakawa et al. ........ 73/204.26 |
| 6,527,835 | B1 * | 3/2003 | Manginell et al. ............. 96/102 |
| 6,666,907 | B1 * | 12/2003 | Manginell et al. .............. 95/87 |
| 6,699,392 | B1 * | 3/2004 | Manginell et al. ........... 210/656 |
| 7,078,237 | B1 * | 7/2006 | Mowry et al. ............... 436/147 |
| 2003/0062263 | A1 * | 4/2003 | Stanford et al. ......... 204/403.01 |
| 2004/0077096 | A1 * | 4/2004 | Nayar et al. ................... 436/57 |

OTHER PUBLICATIONS

Mowry, et al., "Micropyrolyzer for Chemical Analysis of Liquid and Solid Samples", U.S. Appl. No. 10/035,537, filed Oct. 23, 2001.

Lichtenberg et al., "Sample pretreatment on microfabricated devices," *Talanta* 56, 233 (2002).

Manginell, et al., "In-Situ Monitoring of Micro-Chemical Vapor Deposition (m-CVD): Experimental Results and SPICE Modeling," *Tech. Digest 1998 Sol. State Sensor and Actuator Workshop*, 371 (1998).

Manginell, et al., "Selective, pulsed CVD of platinum on microfilament gas sensors," *Tech. Digest 1996 Sol. State Sensor and Actuator Workshop*, 23 (1996).

(Continued)

*Primary Examiner*—Jill Warden
*Assistant Examiner*—Dwayne K Handy
(74) *Attorney, Agent, or Firm*—Kevin W. Bieg

(57) ABSTRACT

A biological preconcentrator comprises a stimulus-responsive active film on a stimulus-producing microfabricated platform. The active film can comprise a thermally switchable polymer film that can be used to selectively absorb and desorb proteins from a protein mixture. The biological microfabricated platform can comprise a thin membrane suspended on a substrate with an integral resistive heater and/or thermoelectric cooler for thermal switching of the active polymer film disposed on the membrane. The active polymer film can comprise hydrogel-like polymers, such as poly(ethylene oxide) or poly(n-isopropylacrylamide), that are tethered to the membrane. The biological preconcentrator can be fabricated with semiconductor materials and technologies.

18 Claims, 4 Drawing Sheets

OTHER PUBLICATIONS

Wunsch, et al., "Recent Advances in AC-DC Transfer Measurements using Thin-Film Thermal Converters," IEEE Trans. on Instrumentation and Measurement, Oct. 2000.

Wunsch, et al., "A New Fabrication Process for Planar Thin-Film Multijunction Thermal Converters," Measurement Science Conf., Anaheim, CA., Jan. 2001.

Ista, et al., "Synthesis of Poly (N-isopropylacrylamide) on Initiatior-Modified Self-Assembled Monolayers," *Langmuir* 17(9), 2522 (2001).

Bunker, et al., "Molecular Switching of Surface Chemistry," invited talk presented at UCLA Chemistry Department Colloquium Series on Jun. 15, 2000.

Bunker, et al., "Switching of Surface Chemistry for Microanalytical Systems," invited talk presented at the Nanoscience and Nanotechnology Symposium held at Pacific Northwest National Laboratory in Richland, Washington on Jun. 21-22, 2000.

Bunker, et al., "Switching of interfacial Energies in Polymeric Coatings," presented at American Vacuum Society Mtg., Boston on Oct. 2-6, 2000.

* cited by examiner

BIOLOGICAL PRECONCENTRATOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates generally to sample pretreatment for microanalytical systems and, more particularly, to a biological preconcentrator for selective absorption and desorption of proteins from a fluid stream.

BACKGROUND OF THE INVENTION

Micrototal analysis systems (μTAS), which have also been termed "chemical laboratories on a chip," are being developed to enable the rapid and sensitive detection of particular chemicals and biochemicals, including pollutants, high explosives, chemical and biological warfare agents, and genomic and proteomic materials. Micrototal analysis systems enable vast improvements in cost, speed, sample and reagent usage, and sample throughput by the integration of fluid manipulation and the different steps of an analytical process into a single microfluidic device. In particular, the microfluidic device seeks to integrate the analytical steps of sample injection, pretreatment, separation, and detection on a single microchip.

A sample to be analyzed generally undergoes sample preparation or pretreatment prior to an actual analysis. Sample pretreatment may involve extracting the sample from a matrix, purification of the sample to remove interferents, derivatization to make the sample more detectable, or analyte preconcentration. In particular, a sample preconcentrator can serve the important function of collecting, purifying, and boosting the concentration of a target analyte to improve detection capability and to discriminate against interferents. Especially for trace analysis, preconcentration of target analytes may enable orders-of-magnitude concentration enhancements, thereby easing separation and detector sensitivity requirements. However, the integration of sample pretreatment into microfluidic devices remains one of the major hurdles to the miniaturization of μTAS. Integration of the sample pretreatment with the microfluidic device is particularly challenging due to the requirement to localize specific analytes from an open flow system and the wide variation and complexity of the samples that need to be analyzed. See e.g., Lichtenberg et al., "Sample pretreatment on microfabricated devices," *Talanta* 56, 233 (2002).

Preconcentrators for μTAS have typically used a passive stationary phase or sorptive medium to retain the analyte for subsequent elution in a more concentrated form. Preferably, the sorptive medium can selectively extract and isolate the target analyte while having a low affinity for other compounds and interferents in the sample stream. Microfluidic systems for manipulating biological fluids have consisted of passive chromatographic media that selectively adsorb solution species, such as proteins, to promote preconcentration or other functions. However, such passive preconcentrators may not provide sufficiently rapid switching to keep up with the fluid flow rate requirements of the separation and detection steps of the μTAS.

The present invention comprises a biological preconcentrator in which the adsorption and desorption processes are actively switched in response to external stimulation. The critical components required to perform the active switching include an active film whose surface properties can be made to change in response to controlled external stimulation and an integrated platform that can provide the appropriate stimulus to the active film within a fluidic environment.

SUMMARY OF THE INVENTION

A biological preconcentrator comprises a platform having a substrate, a suspended membrane formed thereon, and a means for heating the membrane; and an active polymer film disposed on a flow-channel-side of the membrane capable of absorbing at least one protein from a fluidic sample in a flow channel of the platform when the active polymer film is heated above a critical transition temperature. The biological preconcentrator can further comprise a means for cooling the membrane to desorb the at least one protein when the active polymer film is cooled below the critical transition temperature. The active polymer film can comprise a hydrogel-type polymer that is hydrophobic above and hydrophilic below the critical transition temperature.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

A biological preconcentrator comprises a stimulus-responsive active film on a stimulus-producing microfabricated platform. Such active films can comprise stimulus-responsive or 'smart' polymers that undergo strong, nonlinear conformation changes in response to small environmental stimuli (e.g., changes in pH, temperature, ionic strength, or electrical field). A particular class of stimulus-responsive polymers include hydrogels that exhibit reversible swelling behavior and switchable hydrophobic-hydrophilic properties when exposed to small temperature changes about a critical transition temperature. The stimulus-producing platform can comprise a low-power heater (or cooler) on an integrated membrane upon which the thermally responsive polymer is grown. The integrated platform can be configured with fluidic channels to transport analyte-containing fluids over the active polymer film. The temperature control system can preferably provide high heating and/or cooling rates to enable rapid switching of the active polymer film. The active polymer film can thereby rapidly absorb and desorb analytes to keep up with fluid flow rates and separation and detection requirements. This rapid switching can be achieved with the thermally isolated, low mass membrane upon which the heating and/or cooling elements are fabricated.

Figure 1:
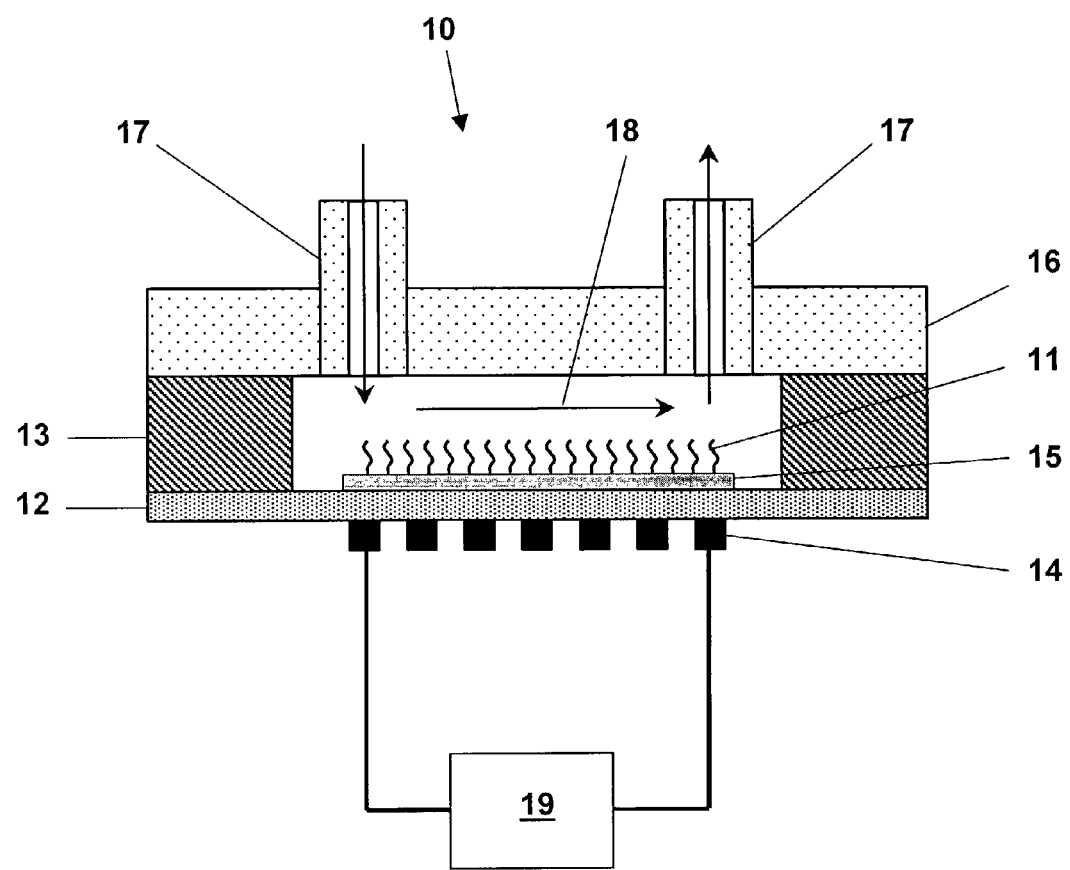
FIG. 1 shows a schematic illustration of a biological preconcentrator comprising a thermally responsive active polymer film on a heated, suspended membrane of a microfabricated platform.

A suitable platform comprises a low-heat capacity, low-loss microhotplate to thermally stimulate an active film on the microhotplate. FIG. 1 is a schematic illustration of an exemplary biological preconcentrator 10 of the present invention that uses a microhotplate platform. The biological preconcentrator 10 comprises an active film 11 disposed on a flow-channel-side of a membrane 12 suspended from a substrate 13 and a resistive heater 14 disposed on the membrane 12 for heating the membrane 12 and the active film 11 attached thereto. The biological preconcentrator 10 can be made of semiconductor-based materials, such as silicon, silicon dioxide, and silicon nitride. Many of the candidate active films 11 of the present invention selectively attach to semiconductor-based materials. If the active film 11 cannot be attached to the membrane material directly, the biological preconcentrator 10 can further comprise a support coating 15 for attachment of the active film 11. The biological preconcentrator 10 can further comprise a sealed lid 16, a fluidic inlet and outlet 17 for flow of the biological mixture into and out a flow channel 18, and a temperature control system 19 to provide electrical current to the resistive heater 14 and control the temperature of the membrane 12 and the active film 11. The biological preconcentrator 10 can be fabricated by material deposition, photolithography, masking, and etching techniques well-known in the semiconductor industry and disclosed in U.S. Pat. No. 6,171,378 and U.S. patent application Ser. No. 10/035,537, which are incorporated herein by reference.

The suspended membrane 12 can be a thin, edge-supported dielectric membrane fabricated on the substrate 13. The substrate 13 can be a silicon wafer. The membrane 12 can be a silicon nitride membrane with thickness of about 1 micron. The thin silicon nitride membrane 12 provides both physical support and electrical insulation for the resistive heater 14 while maintaining good thermal isolation between the resistive heater 14 and the substrate 13. For example, the heat capacity per area of a 0.5 μm-thickness silicon nitride membrane 12 is only $3 \times 10^{-6}$ J/K and the thermal conductivity is only $6 \times 10^{-4}$ W/cmK, enabling extremely rapid heating and cooling. The lateral dimensions of the membrane 12 can range from microns to centimeters. A silicon nitride membrane 12 that is 2 mm on a side can attain a temperature of 200° C. in 6 msec with only 100 mW of electrical heating power.

The resistive heater 14 can be formed by depositing one or more layers of an electrically conductive material on one or both sides of the membrane 12. To facilitate temperature measurement and control, the electrically conductive material preferably comprises a metal with a high temperature coefficient of resistance, such as platinum or tungsten. Separate temperature measurement devices can also be used, such as thermoelectrics, diodes, and thermistors. The resistive heater 14 can comprise a single heating element or multiple heating elements electrically connected in series or in parallel to the power source and temperature controller 19. The resistive heater 14 can be patterned to form a circuitous metal trace, which generally has a serpentine or boustrophedon shape. Alternatively, the resistive heater 14 can be one or more heating elements running the length of the flow channel 18. Alternatively, the resistive heater 14 can be one or more resistive heating elements aligned transverse to the flow direction of the fluid sample.

The active film 11 can comprise a sorptive medium with surface properties that can be made to change in response to controlled external stimulation. The stimulus-responsive sorptive medium can comprise a 'smart' polymer that undergoes strong, nonlinear conformation changes in response to small environmental stimuli (e.g., changes in pH, temperature, ionic strength, or electrical field). For example, the stimulus-responsive polymer can be a hydrogel that exhibits reversible swelling behavior and switchable hydrophobic-hydrophilic properties when exposed to small temperature changes about a critical transition temperature.

Alternative platforms for switching the active film, comprising a thermally isolating low mass support with integral heaters and/or coolers, can be microfabricated with semiconductor industry technologies. For example, a microbridge can be formed by patterning a thin filament of the resistive heater material on a silicon wafer and underetching the filament to leave a microbridge. The switchable active film can be placed in proximity to the thermally isolated microbridge and integrated fluidic channels can be provided for fluid flow of the sample over the active film on the microbridge. See R. P Manginell et al., "In-Situ Monitoring of Micro-Chemical Vapor Deposition (μ-CVD): Experimental Results and SPICE Modeling," *Tech. Digest* 1998 *Sol. State Sensor and Actuator Workshop,* 371 (1998) and R. P Manginell et al., "Selective, pulsed CVD of platinum on microfilament gas sensors," *Tech. Digest* 1996 *Sol. State Sensor and Actuator Workshop,* 23 (1996), both of which are incorporated by reference.

Efficient electrical heating and cooling can be used to trap or release analytes in short duration cycles. With the low-heat capacity, low-thermal-loss biological preconcentrator 10, rapid temperature cycling of the active film 11 can be obtained without active cooling of the membrane 12. Temperature gradients on the membrane 12 can be further controlled by the selective placement of the one or more resistive heaters 14 and peripheral heat sinks to conduct heat locally from the membrane 12.

Alternatively, the biological preconcentrator 10 can further comprise an active cooler. Active cooling may be needed for thermal switching of active films 11 having a critical transition temperature below ambient. For a below-ambient transition temperature, active or passive heating can then be used to heat the actively cooled film above the critical transition temperature. Active cooling also enables an even higher temperature gradient and greater control of the local temperature. Although other types of cooling means can be used with the present invention, thermoelectric cooling is preferable, because it requires no moving parts or refrigerants and the cooling elements can be easily fabricated with the same semiconductor industry technologies used to fabricate the other components of the biological preconcentrator 10.

The thermoelectric cooler can comprise one or more junctions of two different conducting materials, one containing positive charge carriers (p-type) and the other negative charge carriers (n-type). When the p-n junction is reverse-biased (i.e., current flows from the n-type material to the p-type material), the dominant charge carriers move away from the junction and carry away heat, thereby cooling the junction. For high efficiency, the junction materials preferably have a low thermal conductivity, to reduce heat conduction from the substrate to the membrane; small electrical resistivity, to minimize Joule heating; and a high Peltier coefficient (or large Seebeck coefficient), to maximize the heat absorbed. For example, the thermoelectrical junction materials can comprise metallic or semiconductor alloys, such as CuNi, NiCr, or BiSb alloys. The junction materials can be vacuum deposited by evaporation or sputtering and can be patterned to form junctions on one or both sides of the membrane, as is known in the semiconductor industry art. See Wunsch et al., "Recent Advances in AC-DC Transfer Measurements using Thin-Film Thermal Converters," in *IEEE Trans. on Instrumentation and Measurement,* October 2000, and Wunsch et al., "A New Fabrication Process for Planar Thin-Film Multijunction Thermal Converters," presented at the Measurement Science Conference, Anaheim, Calif., January 2001, both of which are incorporated by reference.

Figure 2:
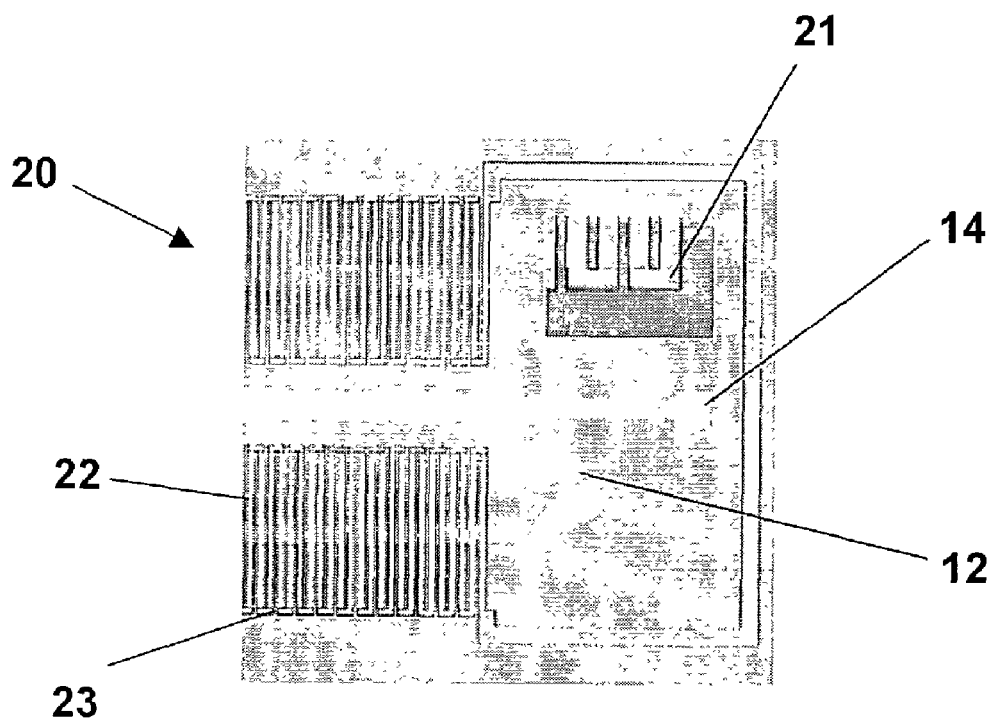
FIG. 2 shows a bottom view of a thermoelectric converter on the suspended membrane for active cooling the active polymer film.

FIG. 2 shows a bottom view of an exemplary actively heated and cooled membrane 12 comprising both a longitudinal resistive heater 14 for heating and a thermoelectric converter 20 for cooling of an active film disposed on the opposite side of the membrane 12. The resistive heater 14 comprises a single, central heating element running the length of the flow channel. The thermoelectric converter 20 can be a thin-film multijunction thermoelectric converter, comprising a plurality of series-connected thermoelectric junctions 21 disposed on the membrane 12 and having electrical leads 22 for current to flow to a heat rejection portion 23 of the thermoelectric converter 20. The thermoelectric junctions 21 can also provide a thermopile sensor to measure the temperature of the membrane 12.

Finite element modeling of the biological preconcentrator 10 indicates that temperature gradients of greater than 0.1° C./micron can be attained with the thermally isolated membrane 12 using localized resistive heating. Even higher local temperature gradients can be achieved by placing the hot junction 21 of a thermoelectric converter 20 adjacent to the cold junction 23 on the membrane 12. Therefore, a thermal zone with a temperature above the transition temperature of the active film 11 can be maintained on the membrane 12 only a few microns from a neighboring thermal zone with a temperature that is below the transition temperature. Excellent temperature localization and resolution of thermal zones can therefore be obtained. Consequently, highly localized concentrations of selected analytes can be achieved with the biological preconcentrator 10 by patterning distinct regions of analyte-adsorbing active film side-by-side in different thermal zones on the same membrane 12. Each thermal zone can be individually temperature programmed due to the thermal isolation obtainable with the biological preconcentrator 10.

A matrix of active zones can thereby be created on a membrane 12 in which both the temperature and active film type are separately controlled. The matrix can comprise a one-dimensional matrix of thermal zones arrayed in the flow direction of a linear membrane. Alternatively, a two-dimensional matrix of thermal zones can be similarly created on a planar membrane, making it possible to separate out many more analytes from a fluid flow. Alternatively, individual membranes can be fabricated adjacent to one-another on the same chip. For example, such a thermally zoned biological preconcentrator enables the collection and detection of multiple proteins from a single sample comprising a mixture of proteins. The selected proteins can then be analyzed directly on the biological preconcentrator with a spatially discriminating detector, such as by fluorescence detection of tagged proteins, or by temperature-programmed release of the proteins to a separator and/or detector.

Figure 3:
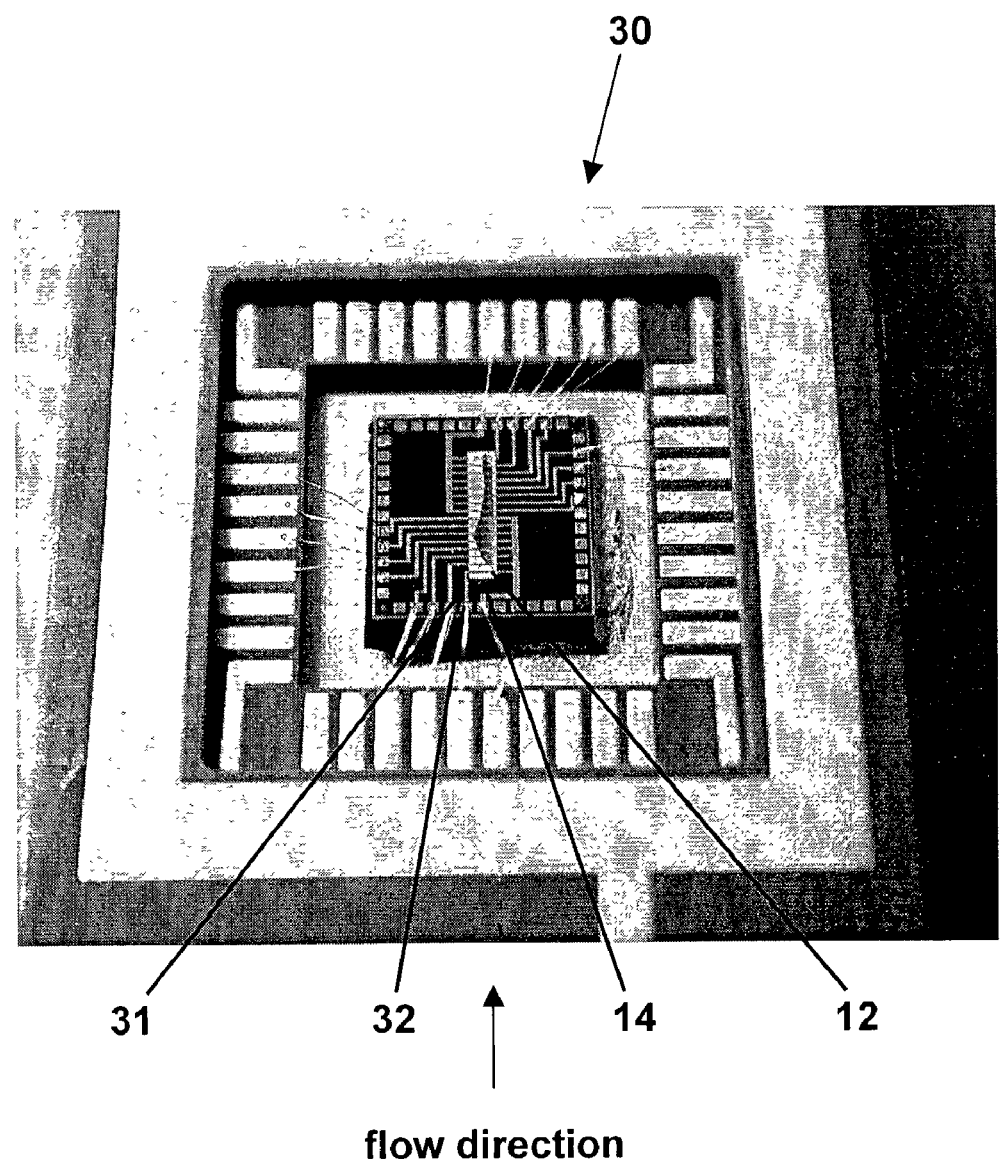
FIG. 3 shows a bottom view of the suspended membrane with independently controlled heating elements transverse to the flow direction of the membrane.

In FIG. 3 is shown a biological preconcentrator 30 with separately controlled thermal zones along the flow direction of the linear membrane 12. The separate thermal zones are achieved by individual resistive heating elements 14 aligned transverse to the flow direction (in the example shown, the resistive heating elements 14 are disposed on the side of the membrane 12 opposite the flow channel 18). The conductive traces 31 from the resistive heating elements 14 can run out to bond pads 32 for electrical connection to a temperature control system (not shown). Individual current control of the resistive heating elements 14 can thereby provide localized thermal zones of the active film 11 disposed on the opposite, flow-channel-side of the membrane 12.

The active film 11 can comprise a hydrogel-type polymer that undergoes a swelling transition in water that is activated by changes in temperature. Temperature-induced changes in the polymer conformation alter the chemistry of the surface to promote adsorption or desorption of analytes contained in fluids in contact with the polymer film. In particular, a temperature-programmed active film 11 containing such a polymer can be used to concentrate target proteins in a dilute protein-containing sample stream for subsequent protein separation and/or analysis.

Hydrogel-type polymers suitable for reversible protein adsorption by the active film 11 include poly(ethylene oxide) (PEO) and poly(n-isopropylacrylamide) (PNIPAM) that exhibit an upper critical solution temperature (UCST) in water. Below the UCST (e.g., 35° C. for PNIPAM), the polymer swells in water to create a hydrophilic surface. Above the UCST, the polymer undergoes a conformation change that collapses the polymer, expels water, and creates a more hydrophobic surface. Globular proteins, such as myoglobin, adhere more strongly to hydrophobic surfaces than hydrophilic ones. Therefore, proteins can be selectively trapped from dilute solutions of proteins mixtures by heating the active polymer film above the UCST. Conversely, the target proteins can be released by cooling the active polymer film below the UCST.

For a practical biological preconcentrator 10, the polymers having an UCST are preferably tethered to the membrane 12 or support coating 15. Otherwise, polymers that are soluble in water below their UCST, such as PNIPAM, would be swept away by fluid in the flow channel 18. A tethered active polymer film 11 can be created on a silicon surface using a surface-initiated polymerization that yields a high graft-density, defect-free polymer monolayer. The surface-initiated polymerization comprises attaching a silane coupling agent containing an initiating pendant group to an oxide layer on the silicon surface and supplying monomer to the initiating pendant group, thereby growing a polymer in situ. The initiating pendant group can comprise any free radical producing moiety, such as an azo or peroxide group. Alternatively, the free radical can be generated from an initiator compound in solution and transferred to a surface-attached silane coupling agent to initiate the polymerization.

Figure 4:
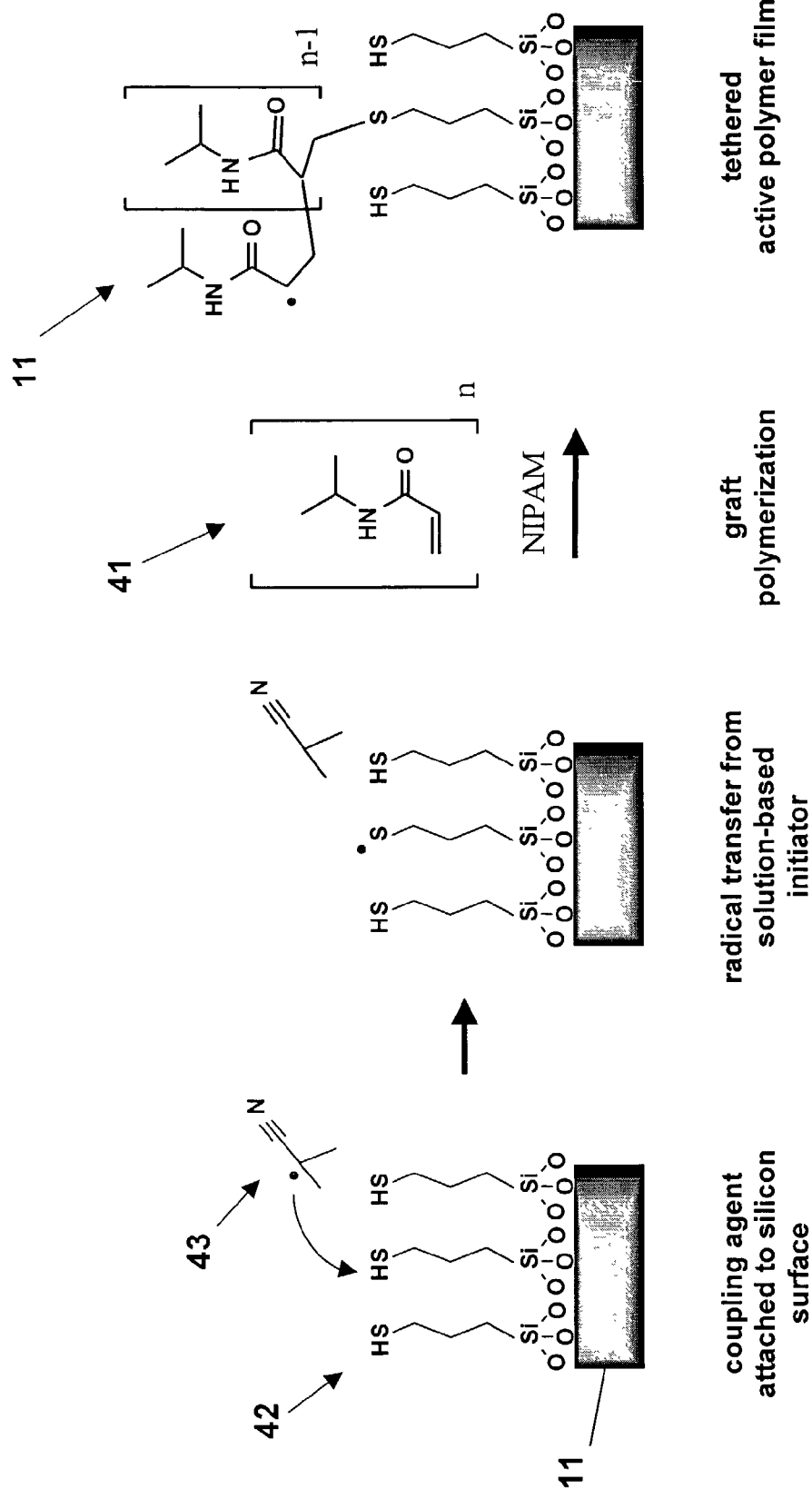
FIG. 4 shows the surface-initiated polymerization of NIPAM to form a tethered film of PolyNIPAM on a silicon membrane.

FIG. 4 shows an example of the formation of a tethered active polymer film 11 by grafting of the hydrogel polymer 41 to a surface-attached silane coupling agent 42 that is activated with a solution-based initiator 43. A tethered PolyNIPAM film can be formed by the azobis(isobutyronitrile)-initiated polymerization of NIPAM on a trimethoxy mercaptopropyl silane monolayer-coated silicon surface. A monolayer of the trimethoxy mercaptopropyl silane coupling agent can be adsorbed onto the silicon surface of the membrane 12 through a standard acid catalyzed deposition. Azobis(isobutyronitrile) (AIBN) initiator can be used as the solution-based free radical generator. Free radicals generated in solution are transferred to trimethoxy mercaptopropyl silane monolayer to form a mercapto radical to initiate the polymerization of PolyNIPAM.

Due to the extremely high chain transfer constant of the mercapto group and the locally high concentration if the silane coupling agent at the silicon surface, the polymerization can be viewed as a surface-bound telomerization that produces a large number of relatively low molecular weight polymers. A pinhole-free active film is preferable to prevent uncontrolled adsorption of protein. The surface telomerization produces an active film with no pinhole defects that would allow protein access to uncoated surface. The reagents are not limited to mercapto group agents, but can include other chain transfer agents on the surface such as halide, amine, carboxylic acid, carbonyl, or hydroxyl groups. Alternative solution-based free-radical generators can include azo, peroxide, persulfate, or other thermal or redox initiators.

Protein is rapidly adsorbed by the active PolyNIPAM film, formed by the above surface telomerization process, when the active PolyPINAM film is locally heated above the UCST of 35° C. The active PolyNIPAM film can be held on the silicon surface for long periods of time without deleterious effects to the protein or the polymer by maintaining the elevated temperature. The absorbed proteins can be analyzed in-situ by fluorescence detection or other means. Alternatively, the underlying membrane can be cooled, swelling the active PolyPINAM film and rapidly releasing the protein in a response time of less than 1 second. The absorbed and preconcentrated protein can thereby be rapidly released to a separation and/or detection element of a μTAS.

The embodiments of the present invention have been described as a biological preconcentrator with a switchable active film layer. It will be understood that the above description is merely illustrative of the applications of the principles of the present invention, the scope of which is to be determined by the claims viewed in light of the specification. Other variants and modifications of the invention will be apparent to those of skill in the art. In particular, the silicon micromachined microhotplate-based biological preconcentrator is just an example of a thermal platform that is suitable for the present invention. Other methods, materials and fabrication technologies can be used to fabricate the biological preconcentrator. For example, conventional machining, plastic fabrication and ceramic technology can also be used. The biological preconcentrator need only to provide a platform to generate localized temperature zones where an active polymer film, such as PolyNIPAM, can trap and release the desired proteins.

We claim:

1. A biological preconcentrator, comprising:
   a platform having a substrate, a suspended membrane formed thereon, and a means for heating the membrane; and
   at least one active polymer film disposed on a flow-channel-side of the membrane that absorbs at least one protein from a fluidic sample in a flow channel of the platform when the at least one active polymer film is heated above a critical transition temperature and desorbs the at least one protein when the at least one polymer film is cooled below the critical transition temperature.

2. The biological preconcentrator of claim 1, wherein the platform comprises semiconductor-based materials.

3. The biological preconcentrator of claim 2, wherein the membrane comprises silicon nitride.

4. The biological preconcentrator of claim 1, wherein the heating means comprises a resistive heater.

5. The biological preconcentrator of claim 4, wherein the resistive heater comprises a plurality of resistive heating elements for independently heating localized thermal zones on the membrane.

6. The biological preconcentrator of claim 5, wherein the plurality of resistive heating elements are aligned transverse to the flow direction of the fluidic sample in the flow channel of the platform.

7. The biological preconcentrator of claim 1, further comprising a means for actively cooling the at least one active polymer film below the critical transition temperature.

8. The biological preconcentrator of claim 7, wherein the cooling means comprises a thermoelectric converter.

9. The biological preconcentrator of claim 8, wherein the thermoelectric converter comprises at least one thermoelectric junction.

10. The biological preconcentrator of claim 9, wherein the at least one thermoelectric junction comprises at least one hot junction and at least one cold junction for heating and cooling localized thermal zones on the membrane.

11. The biological preconcentrator of claim 9, wherein the at least one thermoelectric junction comprises an alloy.

12. The biological preconcentrator of claim 9, wherein the alloy is selected from the group consisting of copper-nickel, nickel-chromium, and bismuth-antimony.

13. The biological preconcentrator of claim 1, further comprising a support coating for attachment of the at least one active polymer film thereto.

14. The biological preconcentrator of claim 1, wherein the at least one active polymer film is hydrophobic above and hydrophilic below the critical transition temperature.

15. The biological preconcentrator of claim 1, wherein the at least one active polymer film comprises a hydrogel.

16. The biological preconcentrator of claim 15, wherein the at least one active polymer film comprises poly(ethylene oxide) or poly(n-isopropylacrylamide).

17. The biological preconcentrator of claim 1, wherein the at least one active polymer film further comprises a silane coupling agent attached to a silicon surface of the membrane and wherein the at least one active polymer film is grafted to the silane coupling agent.

18. The biological preconcentrator of claim 1, wherein the at least one active polymer film is formed by in-situ polymerization on the membrane.

* * * * *